United States Patent [19]

Ikesu et al.

[11] Patent Number: 5,679,506
[45] Date of Patent: Oct. 21, 1997

[54] CYAN COUPLER FOR SILVER HALIDE COLOR PHOTOGRAPHIC LIGHT-SENSITIVE MATERIAL

[75] Inventors: Satoru Ikesu; Rudchenko F. Vladimir; Mitsuhiro Fukuda; Yutaka Kaneko, all of Hino, Japan

[73] Assignee: Konica Corporation, Japan

[21] Appl. No.: 651,802

[22] Filed: May 20, 1996

[30] Foreign Application Priority Data

May 23, 1995 [JP] Japan .................. 7-123794
Jun. 12, 1995 [JP] Japan .................. 7-144504

[51] Int. Cl.⁶ .................................. G03C 7/38
[52] U.S. Cl. ........................................ 430/558
[58] Field of Search ........................ 430/558, 567

[56] References Cited

FOREIGN PATENT DOCUMENTS 0287265  10/1988  European Pat. Off. ........... 430/558
1106057   4/1989  Japan ............................... 430/558
1118132   5/1989  Japan ............................... 430/558

Primary Examiner—Lee C. Wright
Attorney, Agent, or Firm—Jordan B. Bierman; Bierman, Muserlian and Lucas LLP

[57] ABSTRACT

A silver halide color photographic light sensitive material is disclosed, comprising a support having thereon a silver halide emulsion layer containing silver halide grains, wherein said silver halide emulsion layer contains a cyan dye forming coupler represented by the following formula (1) or (2),

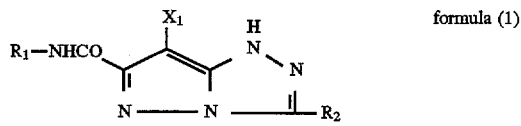

formula (1)

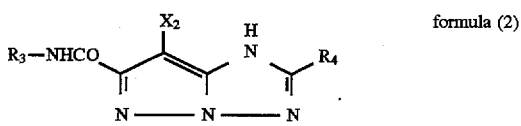

formula (2)

4 Claims, No Drawings

CYAN COUPLER FOR SILVER HALIDE COLOR PHOTOGRAPHIC LIGHT-SENSITIVE MATERIAL

FIELD OF THE INVENTION

This invention relates to a cyan coupler for silver halide color photographic light-sensitive material and, particularly to a cyan coupler for a silver halide color photographic light-sensitive material excellent in color developability and color reproducibility.

BACKGROUND OF THE INVENTION

As for the cyan color image forming couplers, phenols or naphthols have mostly been used so far.

However, the cyan images obtained from the phenols and naphthols having been used so far have had serious problems on color reproduction. The problems have included that an absorption has not been well-defined on the short-wavelength side and that an unnecessary absorption, i.e., an asymmetric absorption, has also been produced in the green spectral region. Due to the problems, the asymmetric absorption has to be corrected by means of a masking in the case of a color negative film and there has not been any asymmetric absorption correcting means in the case of a color negative paper. Therefore, the color reproduction was considerably deteriorated.

Some problems of the preservability have remained unsolved in dye images obtained from phenols and naphthols having been used so far. For example, heat fastness is generally inferior in a dye image obtained from 2-acylaminophenol cyan coupler described in U.S. Pat. Nos. 2,367,531 and 2,423,730; light fastness is generally inferior in a dye image obtained from 2,5-diacylaminophenol cyan coupler described in U.S. Pat. Nos. 2,369,929 and 2,772,162, and both light and heat fastness are generally unsatisfactory in a dye image obtained from 1-hydroxy-2-naphthamido cyan coupler.

Even with a 2,5-diacylaminophenol cyan coupler described in U.S. Pat. No. 4,122,368, Japanese Patent Application Open to Public Inspection (hereinafter referred to as JP OPI Publication) Nos. 57-155538/1982 and 57-157246/1982 and so forth, and a 2,5-diacylaminophenol cyan coupler having a hydroxyl group in the balast portion described in U.S. Pat. No. 3,880,661, each has not yet obtained any satisfactory level for preserving the respective dye images for a long time, from the view points of the fastness against light and heat and a yellow-stain production.

For the purpose of solving the above-mentioned problems, JP OPI Publication Nos. 64-554/1989, 63-250649/1988 and 63-250650/1988 and so forth have proposed the cyan couplers of the pyrazoloazole type.

However, these couplers have introduced an electron-withdrawing group and a hydrogen-bonding group thereinto for satisfying the absorption wavelength of the color dyes to be formed. Therefore, not only the couplers have not been on the level fully satisfying the coupling activity, though a good color reproducibility has been displayed, but also they have not satisfied both color developability and color reproducibility at the same time.

After the present inventors have variously studied by taking the above-mentioned circumstances into consideration, they finally succeeded to discover a pyrazoloazol type cyan coupler excellent in color reproduction and color formation so as to complete the invention.

SUMMARY OF THE INVENTION

It is an object of the invention to provide a cyan coupler for silver halide color photographic light-sensitive material from which an excellent color formation and a sufficient color density can be obtained and a cyan image can also be obtained so as to be excellent in the so-called spectral absorption characteristics including sharp absorption and no unwanted absorption in the blue and green regions.

Another object of the invention is to provide a cyan coupler for silver halide color light-sensitive material capable of forming a cyan image without producing any change of hue against heat and moisture.

The above-mentioned objects of the invention can be achieved with a cyan coupler for silver halide color photographic light-sensitive material, represented by the following formula (1) or (2).

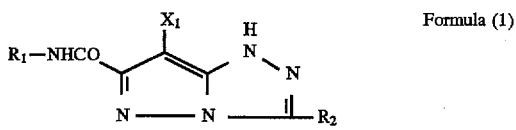

Formula (1)

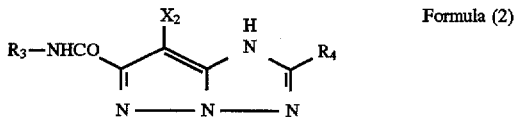

Formula (2)

wherein $R_1$ and $R_3$ represent each a heterocyclic group, alkoxy group, aryloxy group, heterocyclic-oxy group or

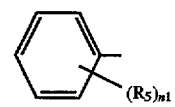

in which $R_5$ represents a substituent and $n_1$ is an an integer of 1 to 5; $R_2$ and $R_4$ represent each a substituent; and $X_1$ and $X_2$ represent each a hydrogen atom or a coupling-off group, which is capable of being released upon reaction with an oxidation product of a color developing agent.

DETAILED DESCRIPTION OF THE INVENTION

In the above-given formulas (1) and (2), the heterocyclic groups represented by $R_1$ and $R_3$ include, for example, 2-thienyl group, 2-furyl group, 1-pyrrolyl group, 2-imidazolyl group, 2-thiazolyl group, 3-isoxazolyl group, 2-pyridyl group, 3-pyridyl group, 2-pyrimidyl group and 3-pyrazolyl group.

The alkoxy groups include, for example, methoxy group, ethoxy group, i-propyloxy group, t-butyloxy group, dodecyloxy group, i-hexadecyloxy group and so forth.

The aryloxy groups include, for example, phenoxy group, naphthyloxy group and so forth.

The heterocyclic-oxy groups include preferably those having a 5- to 7-membered heterocyclic ring including, for example, 3,4,5,6-tetrahydropyranyl-2-oxy group, 1-phenyltetrazole-5-oxy group and so forth.

Among the above-given groups represented by $R_1$ and $R_3$, a heterocyclic group is preferred from the viewpoint of color reproducibility.

Next, there is no special limitation to the substituents represented by $R_2$ and $R_4$. However, they include, exemplarily, each group of alkyl, aryl, anilino, acylamino, sulfonamido, alkylthio, arylthio, alkenyl, cycloalkyl and so forth. Besides the above, the substituents also include, for example, a halogen atom, each group of cycloalkenyl, alkinyl, heterocyclic, sulfonyl, sulfinyl, phosphonyl, acyl, carbamoyl, sulfamoyl, cyano, alkoxy, aryloxy, heterocyclic-oxy, siloxy, acyloxy, sulfonyloxy, carbamoyloxy, amino, alkylamino, imido, ureido, sulfamoylamino, alkoxycarbonylamino, aryloxycarbonylamino, alkoxycarbonyl, aryloxycarbonyl, heterocyclic-thio, thioureido, carboxy, hydroxyl, mercapto, nitro, sulfo and so forth, or also include spiro compound residual group, bridged hydrocarbon residue.

In each of the groups represented by $R_2$ and $R_4$, the alkyl groups are preferably those having 1 to 32 carbon atoms and they may be straight-chained or branched.

As for the aryl group, a phenyl group is preferred.

The acylamino groups include, for example, alkylcarbonylamino group, arylcarbonylamino group and so forth.

The sulfonamido groups include, for example, alkylsulfonylamino group, arylsulfonylamino group and so forth.

The alkyl and aryl components in the alkylthio and arylthio groups include, for example, the alkyl and aryl groups represented by $R_2$ and $R_4$, respectively.

The alkenyl groups include preferably those having 2 to 32 carbon atoms. The cycloalkyl groups include preferably those having 3 to 12 carbon atoms and particularly those having 5 to 7 carbon atoms. The alkenyl groups may be straight-chained or branched.

The cycloalkenyl groups include preferably those having 3 to 12 carbon atoms and particularly those 5 to 7 carbon atoms.

The sulfonyl groups include, for example, alkylsulfonyl group, arylsulfonyl group and so forth; the sulfinyl groups include, for example, alkylsulfinyl group, arylsulfinyl group and so forth;

the phosphonyl groups include, for example, alkylphosphonyl group, alkoxyphosphonyl group, aryloxyphosphonyl group, arylphosphonyl group and so forth;

the acyl groups include, for example, alkylcarbonyl group, arylcarbonyl group and so forth;

the carbamoyl groups include, for example, alkylcarbamoyl group, arylcarbamoyl group and so forth;

the sulfamoyl groups include, for example, alkylsulfamoyl group, arylsulfamoyl group and so forth;

the acyloxy groups include, for example, alkylcarbonyloxy group, arylcarbonyloxy group and so forth;

the sulfonyloxy groups include, for example, alkylsulfonyloxy group, arylsulfonyloxy group and so forth;

the carbamoyloxy groups include, for example, alkylcarbamoyloxy group, arylcarbamoyloxy group and so forth;

the ureido groups include, for example, alkylureido group, arylureido group and so forth;

the sulfamoylamino groups include, for example, alkylsulfamoylamino group, arylsulfamoylamino group and so forth;

the heterocyclic groups include, preferably, those having 5 to 7 membered rings and, exemplarily, 2-furyl group, 2-thienyl group, 2-pirimidinyl group, 2-benzothiazolyl group, 1-pyrrolyl group, 1-tetrazolyl group and so-forth;

the heterocyclic-oxy groups include, preferably, those having 5 to 7 membered rings and, exemplarily, 3,4,5,6-tetrahydropyranyl-2-oxy group, 1-phenyltetrazole-5-oxy group and so forth;

the heterocyclic-thio groups include, preferably, those having 5 to 7 membered rings and, exemplarily, 2-pyridylthio group, 2-benzothiazolylthio group, 2,4-diphenoxy-1,3,5-triazole-6-thio group and so forth;

the siloxy groups include, for example, trimethylsiloxy group, triethylsiloxy group, dimethylbutylsiloxy group and so forth;

the imido groups include, for example, succinimido group, 3-heptadecyl succinimido group, phthalimido group, glutarimido group and so forth;

the spiro compound residual groups include, for example, spiro[3,3]heptane-1-il group and so forth; and the bridged hydrocarbon residue include, for example, bicyclo[2,2,1]heptane-1-il, tricyclo[3,3,1,1$^{37}$]decane-1-i;, 7,7-dimethyl-bicyclo[2,2,1]heptane-1-il and so forth.

Among the above-given substituents represented by $R_2$ and $R_4$, alkyl groups, aryl groups and heterocyclic groups are preferred and, inter alia, aryl groups are particularly preferred, from the viewpoint of color reproducibility.

The above-given groups are also allowed to have such a further substituent as a ballast group including, for example, a long-chained hydrocarbon group, a polymer residual group and so forth.

The afore-mentioned substituent, R5 has the same as defined in $R_2$ and $R_4$.

$X_1$ and $X_2$ represent each a hydrogen atom or a coupling-off group capable of being released upon reaction with the oxidation product of a color developing agent. The coupling-off groups capable of being released upon reaction with an oxidation product of the color developing agent include, for example, a halogen atom (such as a chlorine atom, a bromine atom, a fluorine atom and so forth) and each of the groups of alkoxy, aryloxy, heterocyclic-oxy, acyloxy, sulfonyloxy, alkoxycarbonyloxy, aryloxycarbonyl, alkyloxalyloxy, alkoxyoxalyloxy, alkylthio, arylthio, heterocyclic-thio, alkyloxythiocarbonylthio, acylamino, sulfonamido, nitrogen-containing heterocyclic ring coupled with an N atom, alkyloxycarbonylamino, aryloxycarbonylamino, carboxyl and so forth. Among them, a hydrogen atom, a halogen atom, an alkoxy group, an aryloxy group, a heterocyclic-oxy group, an alkylthio group, an arylthio group, a heterocyclic-thio group, a nitrogen-containing heterocyclic group coupled with an N atom and so forth.

Among the cyan couplers for silver halide color photographic light-sensitive material represented by Formula (1) or (2) of the invention, those represented by Formula (1) are preferable from the viewpoint of color reproducibility.

A cyan coupler represented by the following formula (3) is more preferable.

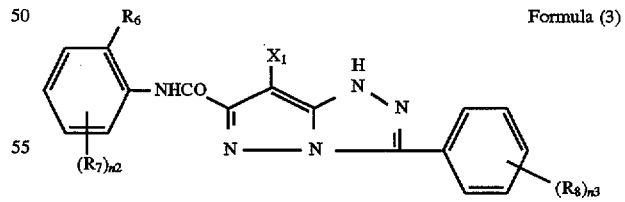

Formula (3)

In the formula, $R_6$ represents a substituent; $R_7$ and $R_8$ each represent a hydrogen atom or a substituent; $n_2$ is an integer of 1 to 4, and $n_3$ is an integer of 1 to 5; and $X_1$ is the same as defined in the formula (1).

Now the typical examples of the compounds of the cyan couplers for silver halide color photographic light-sensitive material represented by Formula (1) or (2) of the invention will be given below. However, the invention shall not be limited thereto.

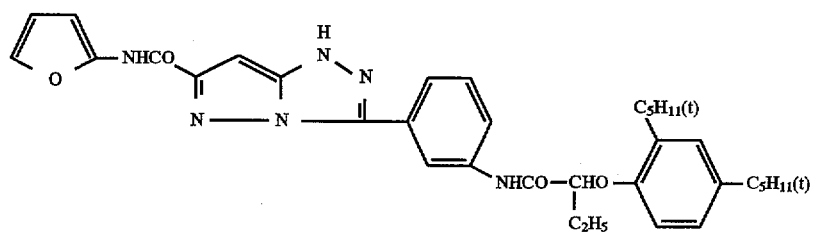
I-1
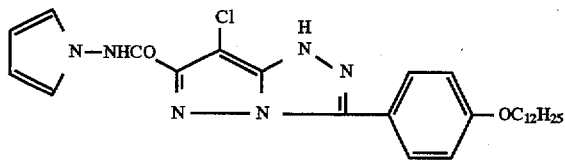
I-2
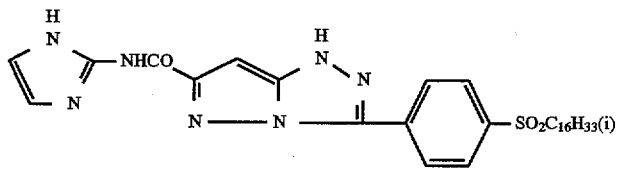
I-3
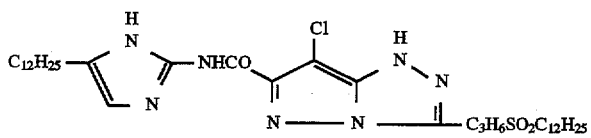
I-4
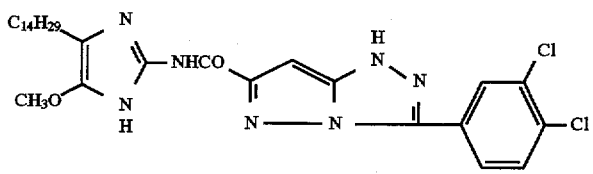
I-5
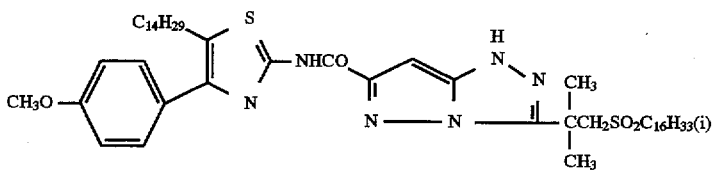
I-6
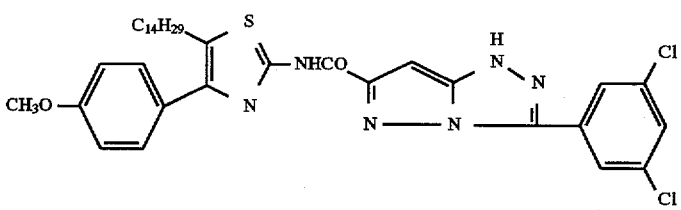
I-7
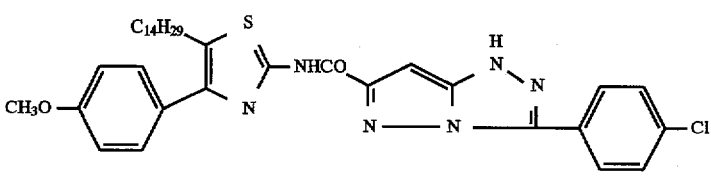
I-8
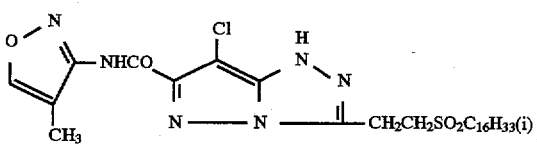
I-9

-continued
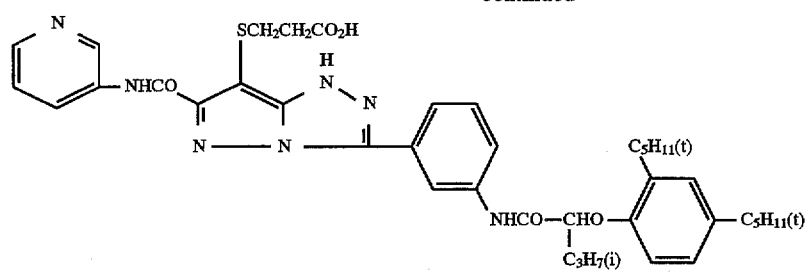
I-10
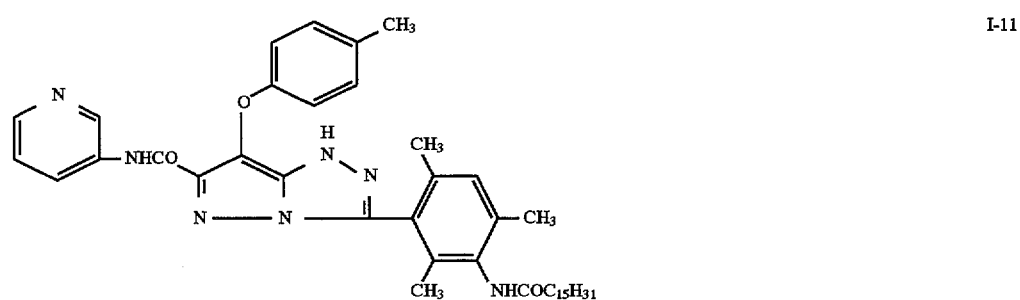
I-11
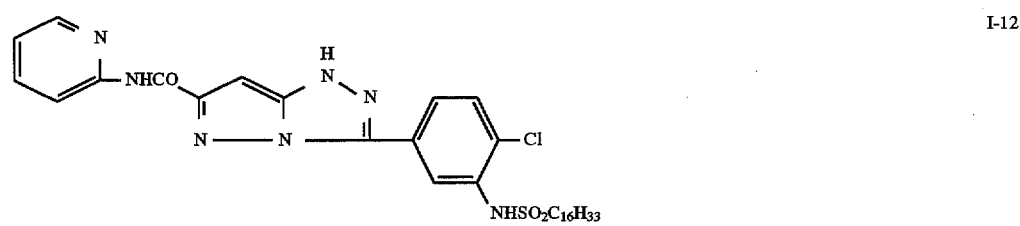
I-12
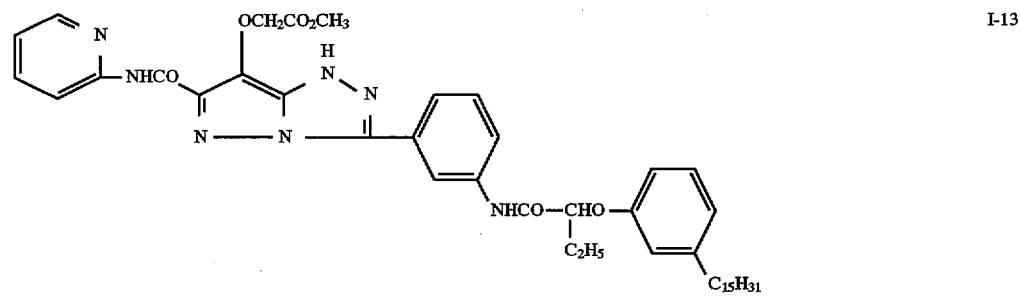
I-13
I-14
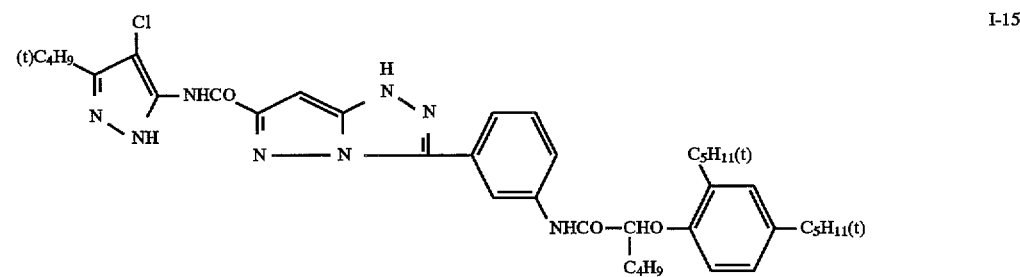
I-15

-continued
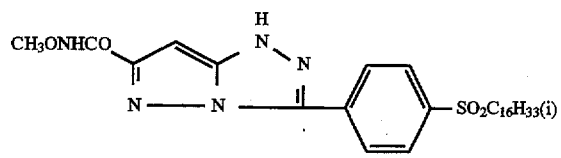
I-16
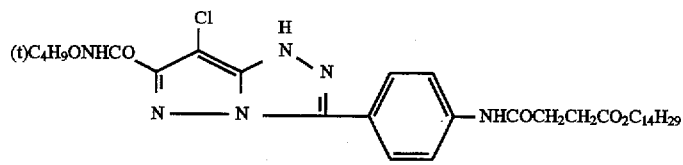
I-17
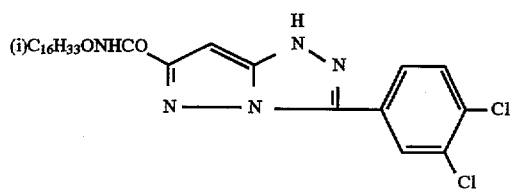
I-18
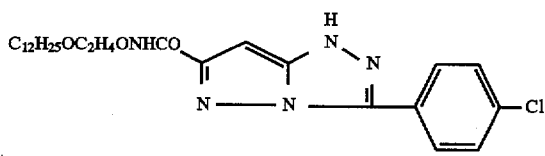
I-19
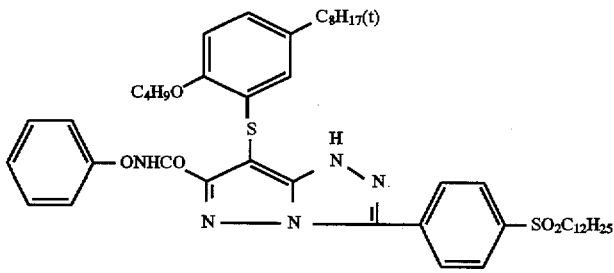
I-20
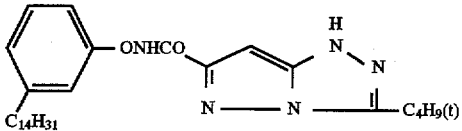
I-21
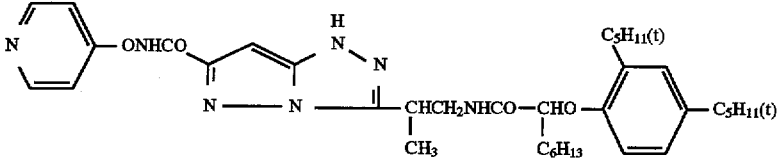
I-22
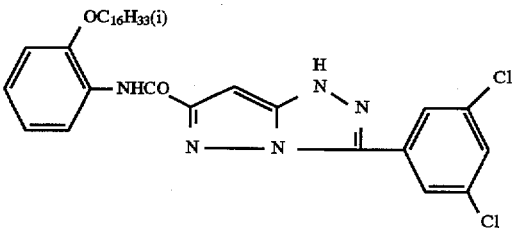
I-23

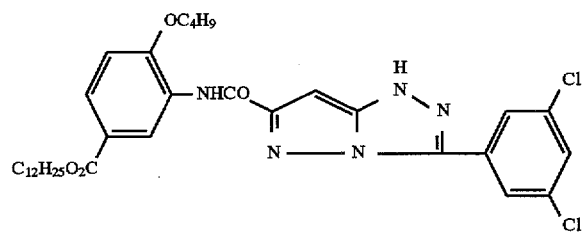
I-24
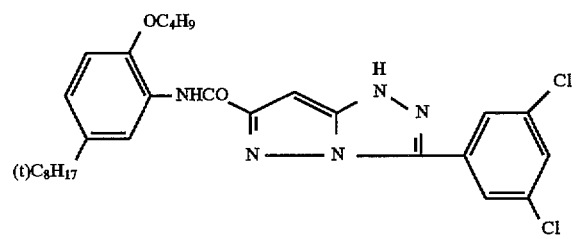
I-25
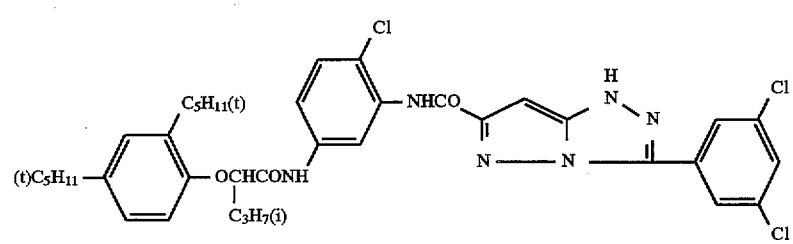
I-26
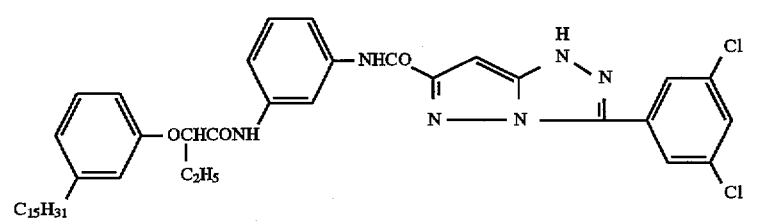
I-27
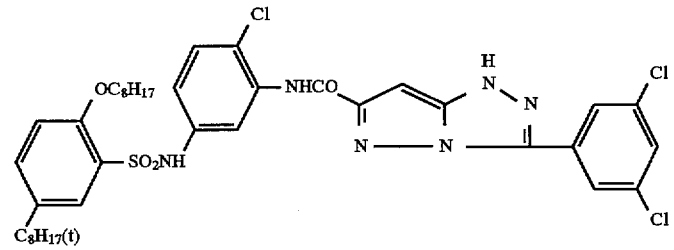
I-28
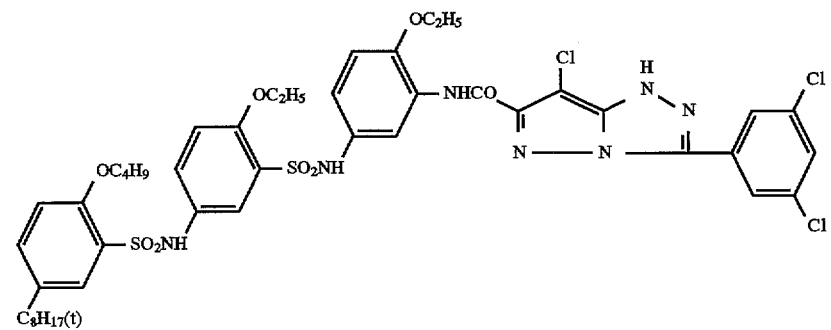
I-29

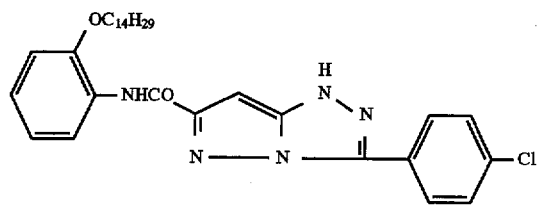
I-30
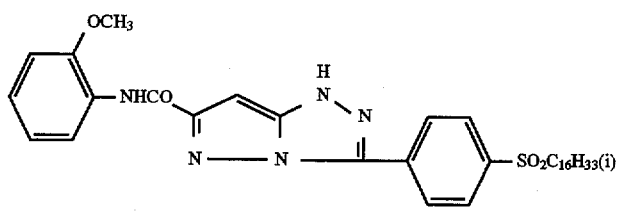
I-31
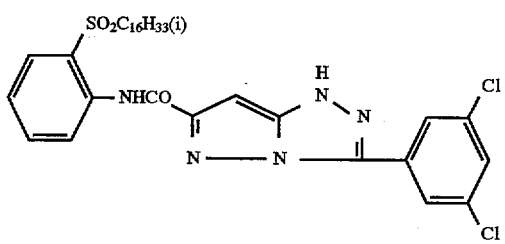
I-32
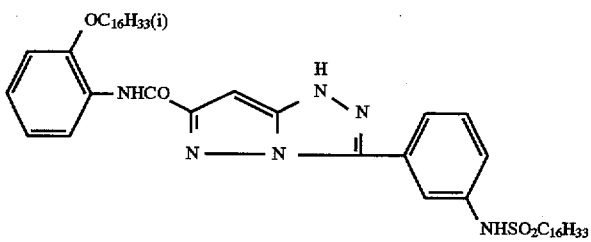
I-33
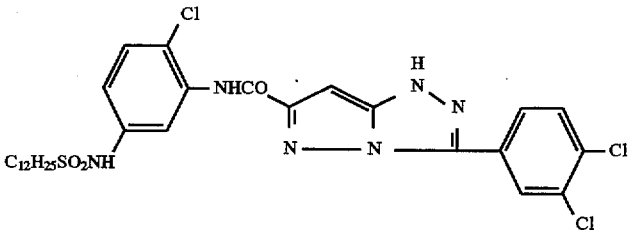
I-34
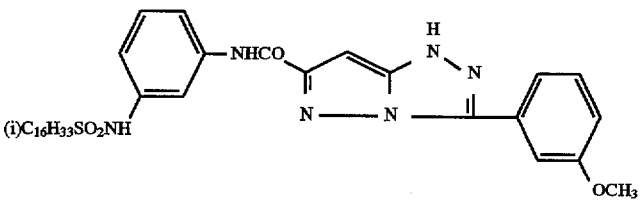
I-35
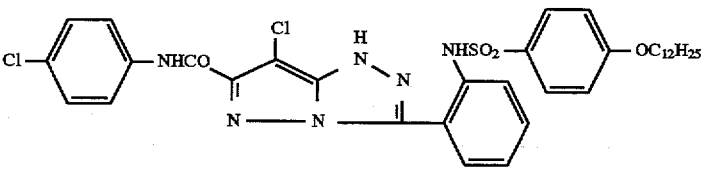
I-36

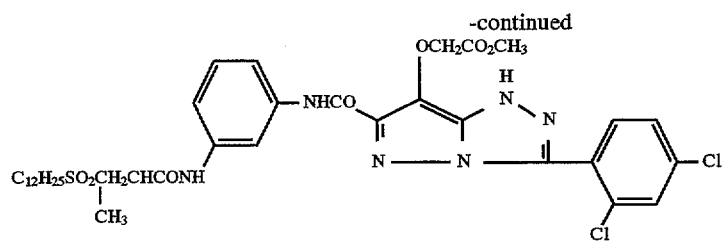
I-37
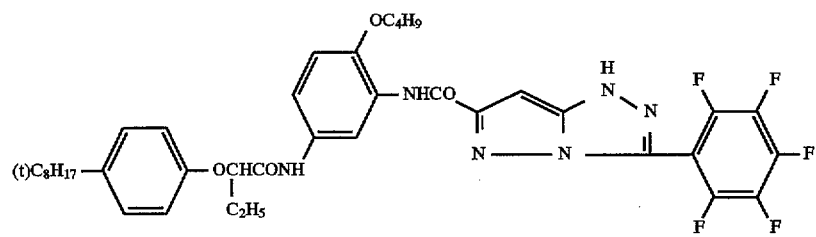
I-38
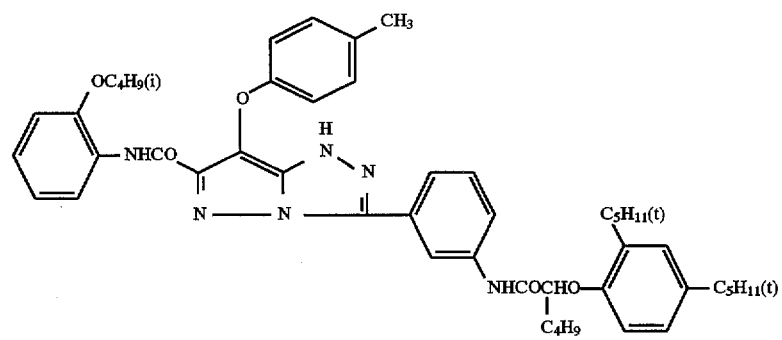
I-39
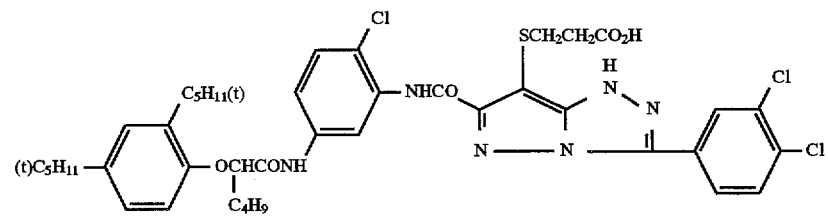
I-40
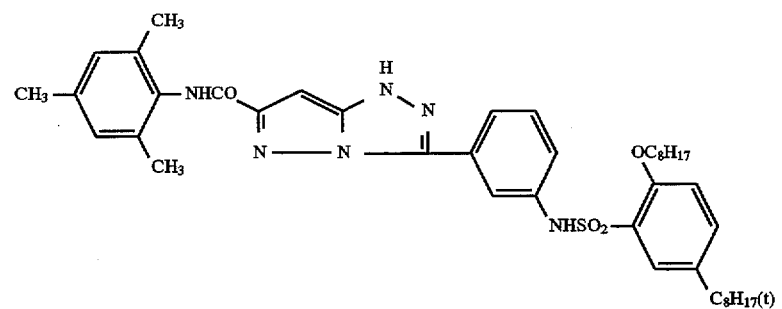
I-41
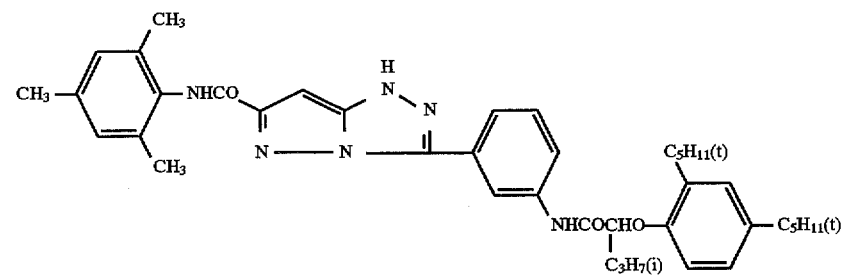
I-42

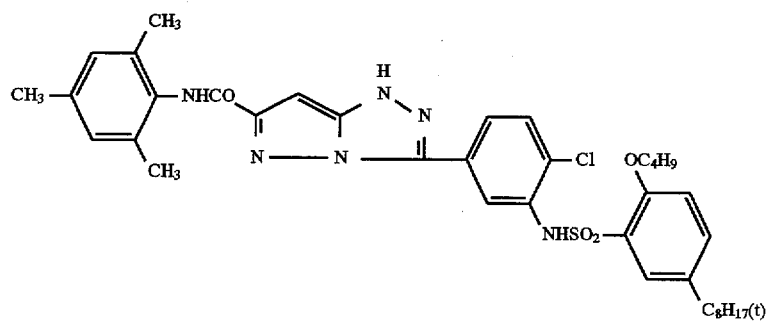
I-43
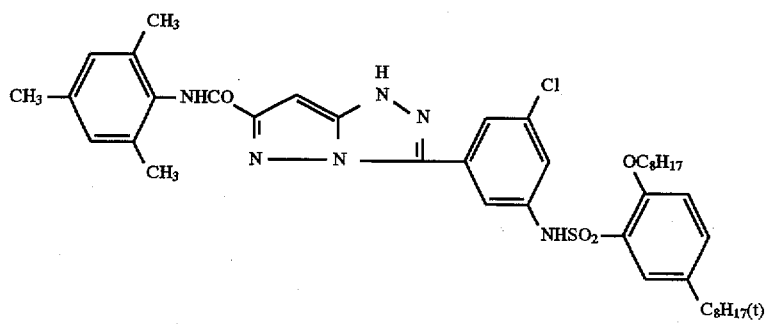
I-44
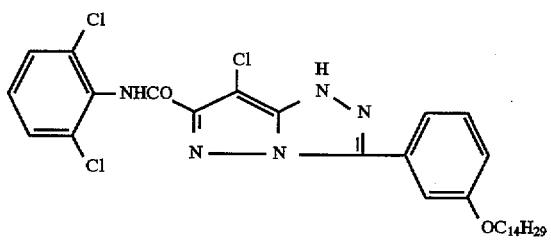
I-45
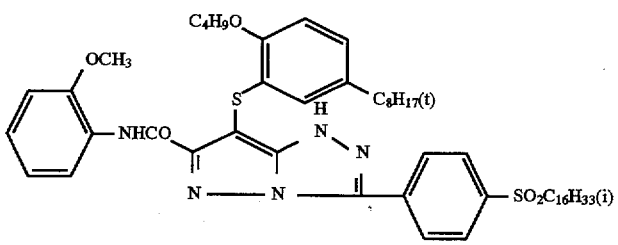
I-46
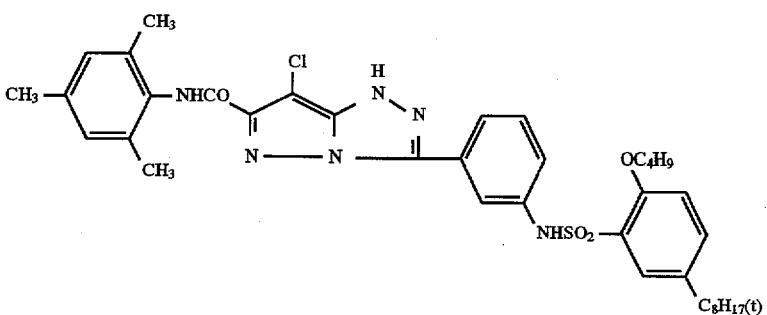
I-47

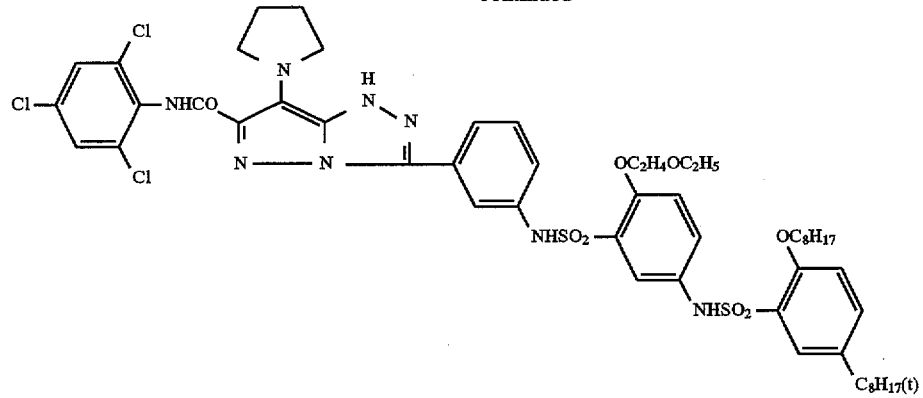
I-48
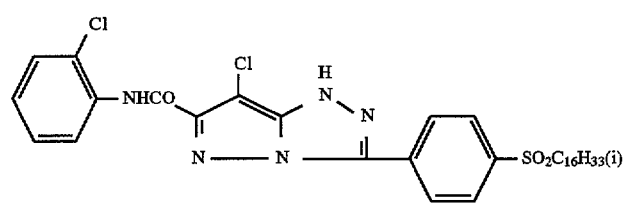
I-49
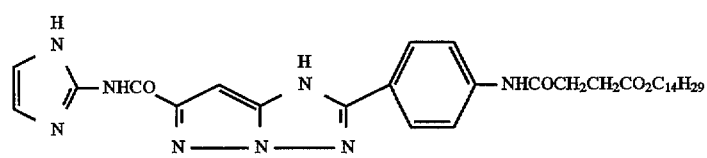
II-1
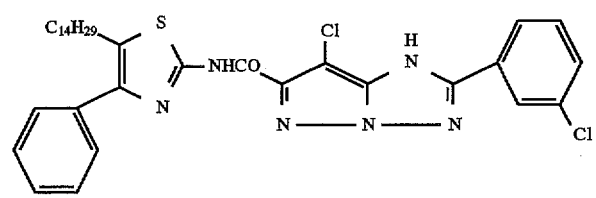
II-2
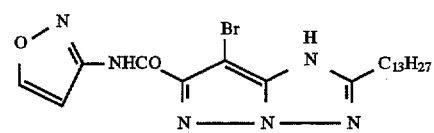
II-3
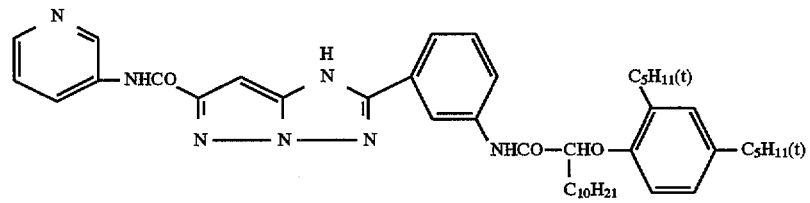
II-4
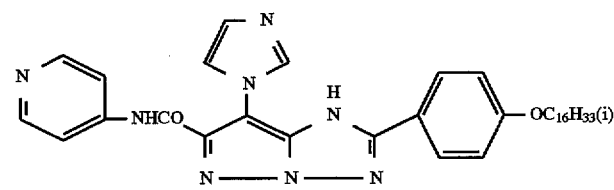
II-5
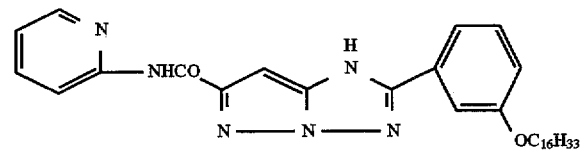
II-6

-continued
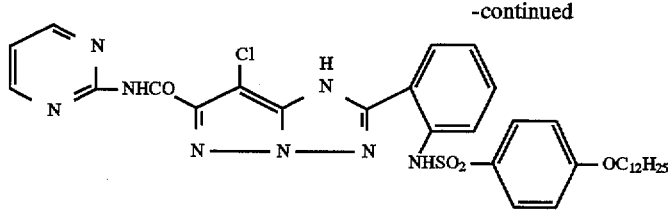
II-7
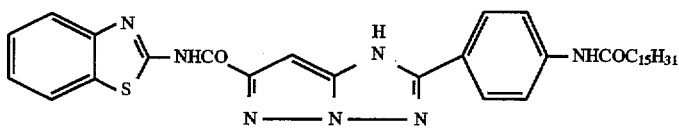
II-8
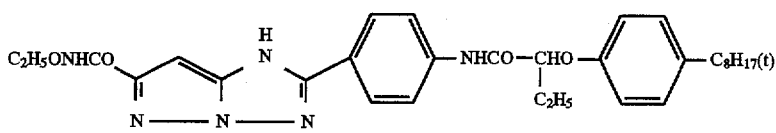
II-9
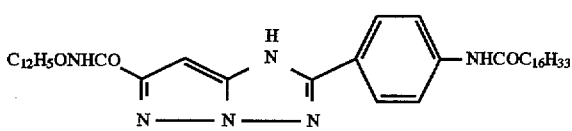
II-10
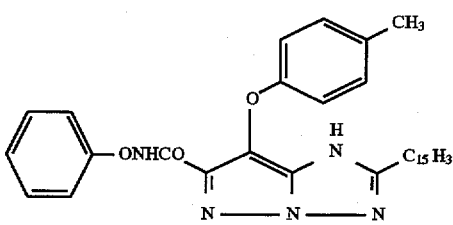
II-11
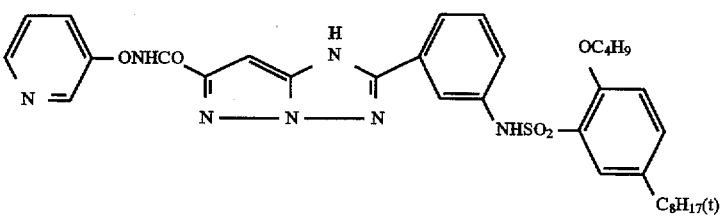
II-12
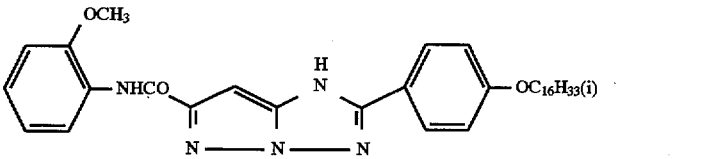
II-13
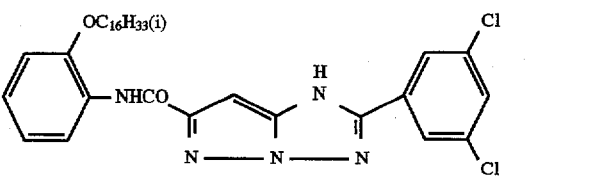
II-14
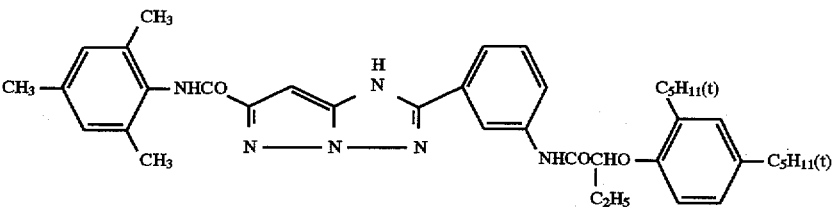
II-15

-continued
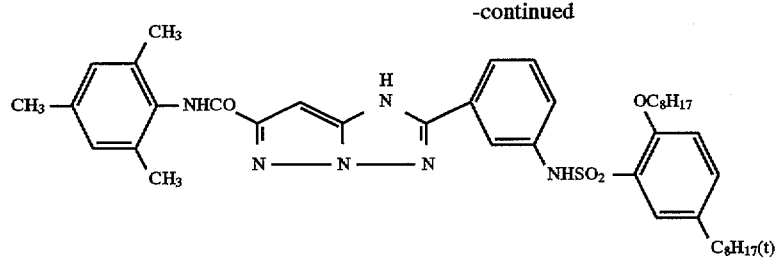
I-16
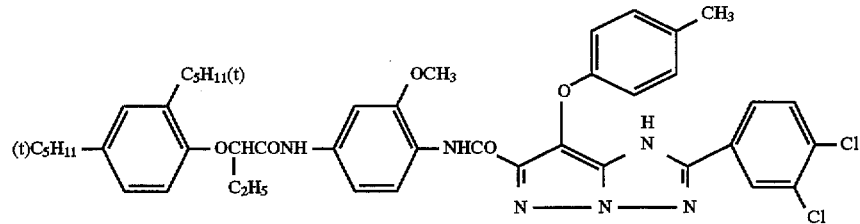
I-17
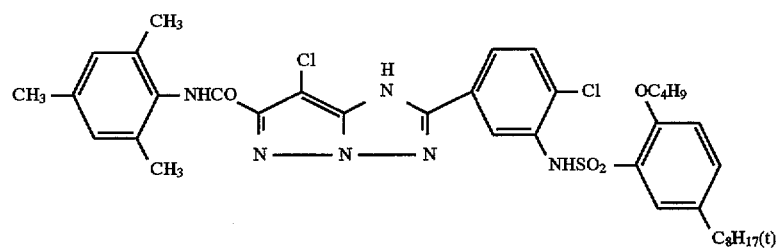
I-18
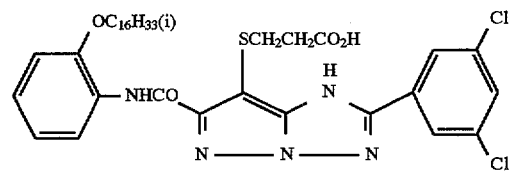
I-19
The examples of synthesizing the cyan couplers of the invention will be shown below.
<Synthesis of Exemplified Compound I-7>
Synthesizing scheme
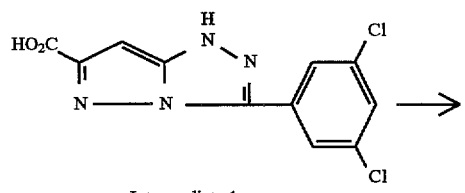
Intermediate 1
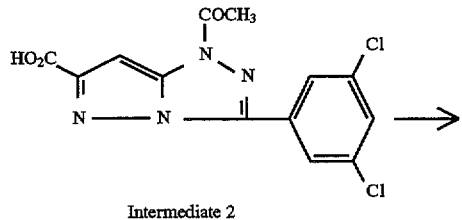
Intermediate 2

-continued
<Synthesis of Exemplified Compound I-7>
Synthesizing scheme

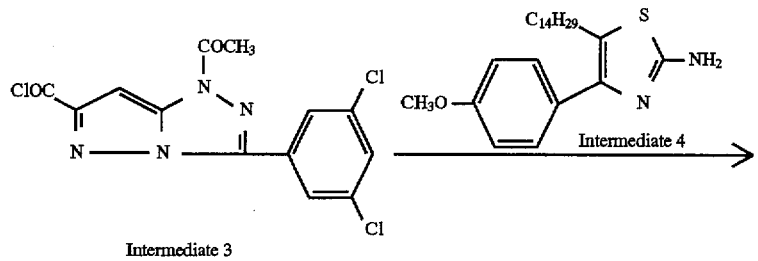

Exemplified Compound I-7

(i) Synthesis of Intermediate 2

While stirring 175 g (0.59 mol) of intermediate 2, 1.2 liters of pyridine and 66 g (0.65 mol) of acetic acid anhydride, they were reacted together at room temperature for 5 hours. After completing the reaction, the resulting crystals were filtrated and were then dispersed in 1.6 liters of 5% hydrochloric acid. After about 30 minutes, the resulting crystals were filtrated and were then washed, so that 190 g of intermediate 2 were obtained. (yield of 95%)

(ii) Synthesis of Intermediate 3

Intermediate 2 of 150 g (0.44 mol) was dispersed in 900 ml of chloroform and thereto 163 g (1.37 mol) of thionyl chloride and 30 ml of pyridine were added in this order. The resulting solution was reacted for 6 hours while heating and refluxing it. After completing the reaction, the remaining solvent was distilled away under reduced pressure, so that 166 g of intermediate 3 was obtained. (yield of 106%) Intermediate 3 was not further refined, but it was used as it was in the next reaction.

(iii) Synthesis of Exemplified Compound I-7

Intermediate 3 of 3.58 g (0.01 mol) was dissolved in 30 ml of pyridine and 4.02 g (0.01 mol) of intermediate 4 was then added thereto. The resulting solution was reacted at room temperature for 8 hours. After completing the reaction, 20 ml of aqueous solution of 4.15 g (0.03 mol) of potassium carbonate was added thereto and the resulting solution was reacted for 2 hours while heating and refluxing it.

After completing the reaction, ethyl acetate was added thereto and the extraction, washing, drying and condensation were carried out. Thereafter, the resulting residue was refined in column chromatography, so that 3.89 g of the objective exemplified compound I-7 was obtained. (The yield=57%)

The structure thereof was confirmed in $^1$H-NMR, IR and MASS spectrography.

Synthesis of Exemplified Compound (I-41)

Synthesis scheme $$H_2NHNCNHNH_2 + BrCH_2COCO_2C_2H_5 \longrightarrow$$
$$\quad\;\; \overset{S}{\|}$$
41a 41b -continued
Synthesis scheme

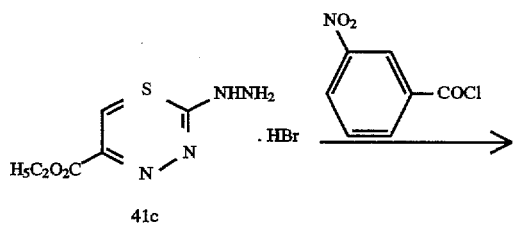
41c

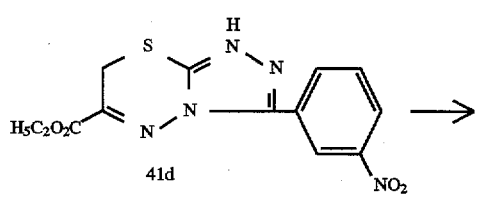
41d

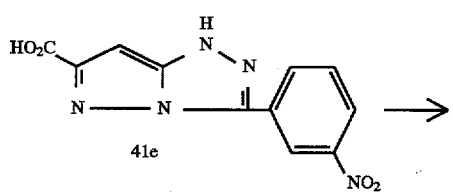
41e

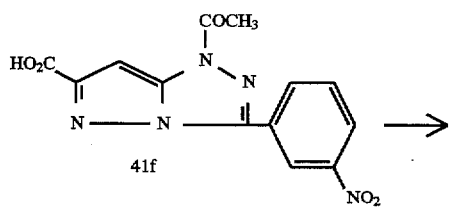
41f

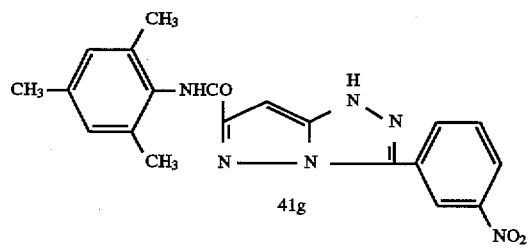
41g

-continued
Synthesis scheme

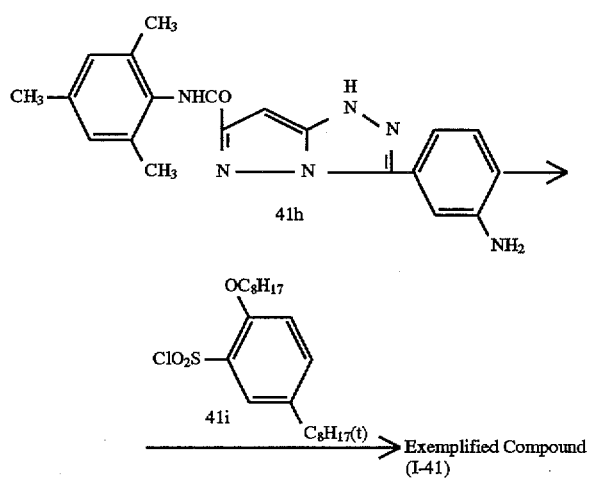

(i) Synthesis of Intermediate (41c)

Intermediate (41a) of 80 g (0.75 mol) was dispersed in 750 ml of ethanol, and intermediate (41b) of 147 g (0.75 mol) was added thereto under ice-cooling. The reaction mixture was further stirred at a room temperature and after being ice-cooled, the resulting crystals were filtered to obtain an intermediate (41c) of 157 g (yield, 74%) with a melting point of 142° to 143° C.

(ii) Synthesis of Intermediate (41d)

The intermediate (41c) of 150 g (0.53 mol) was dispersed in 750 ml of acetonitrile and 99.9 g of 3-nitrobenzoyl chloride (0.53 mol) was added thereto and the mixture was reacted for 3 hours while being heated under reflux. The resulting crystals were extracted with ethyl acetate and sodium carbonate aqueous solution after drying, solvent was removed by distillation. The residue was recrystalized in ethanol to obtain an intermediate (41d) of 134 g (yield of 76%).

(iii) Synthesis of Intermediate ((41e)

The intermediate (41d) of 66.7 g (0.2 mol) was reacted in anhydrous acetic acid for 3.5 hours while being heated and refluxed. Anhydrous acetic acid was distilled away under reduced pressure and were added thereto 480 ml of acetic acid, 105 ml of concentrated hydrochloric acid and 25 ml of 32–36% hypophosphorous acid. The mixture was reacted for 4 hours while being heating under reflux and, after allowed to stand for cooling, the resulting crystals were filtered. The crystals were heated under reflux for 4 hours in acetic acid of 400 ml, water of 30 ml and concentrated sulfuric acid of 20 ml. The reaction solution was poured into water of 500 ml and the resulting crystals was filtered and washed with water and ethyl acetate to obtain an intermediate (41e) of 52.5 g (yield of 96%).

(iv) Synthesis of Intermediate (41f)

The intermediate (41e) of 52.4 g (0.192 mol) was dispersed in 250 ml of pyridine and anhydrous acetic acid of 23.5 g (0.23 mol) was added thereto under being ice-cooled. The mixture was allowed to be reacted for overnight at room temperature.

Thereafter, the reaction mixture was poured into diluted hydrochloric acid and the resulting crystals was filtered, washed and dried to obtain an intermediate (41f) of 57.5 g (yield of 95%).

(v) Synthesis of intermediate (41g)

The intermediate (41f) of 6.3 g (20 mmol was dispersed in 30 ml of chloroform and pyridine of 1.58 g (20 mmol) and thiony chloride of 1.9 g (0.1 mol) was added thereto at 0° C. under ice-cooling. The mixture was reacted at room temperature for 1.5 hours and then, solvent was distilled away under reduced pressure.

To the resulting residue was added 50 ml of pyridine containing mesitylamine of 2.97 g (22 mmol) at 0° C. under ice-cooling and the mixture was allowed to be reacted at room temperature.

Thereafter, 35 ml of a 20% potassium carbonate aqueous solution was added thereto and the mixture was allowed to be reacted for 1 hour while being heated under reflux.

After cooling, ice-cooled dilute hydrochloric acid was poured thereto and the resulting crystals were filtered, washed and dried to obtain an intermediate (41g) of 7.8 g (yield of 100%).

(vi) Synthesis of Intermediate (41h)

The intermediate (19 g) of 1.17 g (3 mmol) was reacted in anhydrous tin (II) chloride of 2.84 g (15 mmol) and 20 ml of ethanol while being heated under reflux for 0.5 hour. After completing reaction, the reaction mixture was poured into water and the resulting crystals were filtered, washed with an aqueous solution of sodium carbonate and extracted with tetrahydrofuran. After drying, solvent was removed by distillation under reduced pressure to obtain an intermediate (41h) of 0.64 g (yield of 62%).

(vii) Synthesis of Exemplified Compound (I-41)

The intermediate (41h) of 0.67 g (1.86 mmol) was dissolved in 10 ml of pyridine and thereto was added an intermediate (41i) of 0.77 g (1.86 mmol) at room temperature. Thereafter, the mixture was allowed to be reacted overnight.

The reaction solution was poured into a diluted hydrochloric acid solution and the resulting crystals were filtered. The crystal were recrystalized in ethyl acetate to obtain exemplified compound (I-41) of 0.60 g (yield of 44%) wit a melting point of 141°–143° C. The structure thereof was confirmed by $^1$H-NMR, IR and MASS spectrography.

The couplers of the invention may be used ordinarily in an amount within the range of $1\times10^{-3}$ mols to 1 mol and preferably $1\times10^{-2}$ mols to $8\times10^{-1}$ mols per mol of a silver halide used.

The couplers of the invention may also be used together with the other kinds of cyan couplers.

Any means and techniques applicable to any ordinary dye-forming couplers may similarly be applied to the couplers of the invention.

In any color development processes, the couplers of the invention may be used therein as a raw material for forming a color photograph. The color development processes include typically a coupler-in-developer type color development process and a coupler-in-emulsion type color development process. When making use of a coupler-in-developer type process, a coupler of the invention may be used by dissolving it in an aqueous alkaline solution or an organic solvent (such as alcohol) and then by adding the resulting solution to a developing solution.

When making use of a coupler of the invention as a raw material for forming a color photograph in a coupler-in-emulsion type color development process, the coupler of the invention may be used by containing it in a photographic light-sensitive material.

Typically, it is preferable to use a process for forming a color light-sensitive material, in which a coupler of the invention is compounded in a silver halide emulsion and the resulting emulsion is coated on a support.

A coupler of the invention is used in a color photographic light-sensitive material such as a color negative or positive film and a color printing paper.

A light-sensitive material applied with a coupler of the invention, including the above-mentioned color printing paper, may be of the monochromatic type or the multicolored type. In a multi-color type light-sensitive material, a coupler of the invention may be contained in any layer. It is, however, ordinarily contained in a green-sensitive silver halide emulsion layer or/and a red-sensitive silver halide. A multi-colored light-sensitive material has a dye image-forming component unit having light-sensitivity in each of the three primary color regions. Each of the component units can be comprised of a single or multilayered emulsion layer each light-sensitive to a certain region having a spectrum. The constitutional layers of a light-sensitive material, including an image-forming component unit layer, may be arranged in various orders having been known in the art.

A typical multi-color type light-sensitive material is comprised of a support having thereon a cyan dye image forming component unit comprising at least one red-sensitive silver halide emulsion layer containing at least one cyan coupler (in which at least one cyan coupler is that of the invention), a magenta dye image forming component unit comprising at least one green-sensitive silver halide emulsion layer containing at least one magenta coupler, and a yellow dye image forming component unit comprising at least one blue-sensitive silver halide emulsion layer containing at least one yellow coupler.

The above-mentioned light-sensitive material may have such an additional layer as a filter layer, an intermediate layer, a protective layer or a subcoated layer.

A coupler of the invention may be contained in an emulsion in the manner known so far. For example, the couplers of the invention are dissolved independently or in combination in a high-boiling organic solvent having a boiling point of not lower than 175° C. such as tricresyl phosphate and dibutyl phthalate or a low-boiling solvent such as butyl propionate independently, respectively or, if required, in the mixed solution of the above-mentioned solvents. After that, the resulting solution is mixed with an aqueous gelatin solution containing a surfactant and the mixture is then emulsified by a high-speed rotary mixer or a colloid mill. The resulting emulsion is added to silver halide, so that a silver halide emulsion applicable to the invention can be prepared.

The silver halide preferably applicable to a light-sensitive material applied with a coupler of the invention include, for example, silver chloride, silver chlorobromide and silver chloroiodobromide. Further, a compounded mixture of silver chloride and silver bromide may also be used. To be more concrete, in the case where a silver halide emulsion is used in a color printing paper, a particularly speedy developability is required. Therefore, it is preferable to contain therein a chlorine atom as a halogen component of the silver halide and it is particularly preferable that the silver halide is silver chloride, silver chlorobromide or silver chloroiodobromide each containing at least 1% of silver chloride.

A silver halide emulsion is chemically sensitized in an ordinary process, and it may also be optically sensitized to be in any desired wavelength region.

For the purpose of preventing a fog from producing in the courses of manufacturing, preserving or processing a light-sensitive material and/or stabilizing the photographic characteristics of the light-sensitive material, it is allowed to add a compound having been known in the photographic industry as an antifoggant or a stabilizer.

A color light-sensitive material applied with a coupler of the invention may be applied with an anti-color-foggant, a dye-image stabilizer, a UV absorbent, an antistatic agent, a matting agent, a surfactant and so forth which may commonly be used.

The above-given additives may be referred to the description of Research Disclosure Vol. 176, pp. 22–31, Dec., 1978.

An image can be formed when a color photographic light-sensitive material applied with a coupler of the invention is treated in a color-development process having been well-known in the art.

A color photographic light-sensitive material applied with a coupler relating to the invention contains a color developing agent in the form of itself or the precursor thereof in the hydrophilic colloidal layer of the light-sensitive material, and the light-sensitive material can be treated in an alkaline activation bath.

A color photographic light-sensitive material applied with a coupler of the invention is color-developed and is then subjected to bleaching and fixing treatments. The bleaching and fixing treatments may also be carried out at the same time.

After completing the fixing treatment, a washing treatment is usually carried out. A stabilizing treatment may be carried out in place of the washing treatment, and the two treatments may be carried out in combination.

EXAMPLES

Now, the invention will concretely be detailed with reference to the following examples. However, the invention shall not be limited thereto.

Example 1

On a paper-made support laminated with polyethylene on the both side thereof, each of the following layers was coated in order from the support side, so that red-light sensitive color light-sensitive material sample 1 could be prepared. Hereinafter, the amounts of the compounds added will be shown in terms of an amount per sq. meter, unless otherwise expressly stated, (provided that silver halide will be shown in terms of the silver content thereof.)

Layer 1: an emulsion layer

A red-sensitive emulsion layer comprising $9.1 \times 10^{-4}$ mols of comparative cyan coupler a prepared by dissolving in 0.45 g of dioctyl phthalate, 1.3 g of gelatin and 0.2 liters of an red-sensitive silver chlorobromide emulsion (containing 99.5 mol % of silver chloride).

Layer 2: a protective layer

A protective layer containing 0.50 g of gelatin. Thereto, sodium 4-dichloro-6-hydroxy-s-triazine was added in an amount of 0.017 g per g of gelatin.

Next, samples 2 through 14 of the invention were prepared in the same manner as in Sample 1, except that comparative coupler a was replaced respectively by the couplers shown in Table 1.

The resulting Samples 1 through 14 were exposed to light through a wedge in an ordinary method and were then developed in the following development process.

| (Development process) | | |
|---|---|---|
| Processing step | Temperature | Time |
| Color developing | 35.0 ± 0.3° C. | 45 sec. |
| Bleach-fixing | 35.0 ± 0.5° C. | 45 sec. |
| Stabilizing | 30° C. to 34° C. | 90 sec. |

-continued

| (Development process) | | |
|---|---|---|
| Processing step | Temperature | Time |
| Drying | 60° C. to 80° C. | 60 sec. |

The compositions of the processing solutions used in each of the processing steps were as follows.

| (Color developer) | |
|---|---|
| Water | 800 ml |
| Triethanol amine | 10 g |
| N,N-diethyl hydroxylamine | 5 g |
| Potassium bromide | 0.02 g |
| Potassium chloride | 2 g |
| Potassium sulfite | 0.3 g |
| 1-Hydroxyethylidene-1,1-diphosphonic acid | 1.0 g |
| Ethylenediamine tetraacetic acid | 1.0 g |
| Disodium catechol-3,5-disulfonate | 1.0 g |
| Diethylene glycol | 10 g |
| 3-Methyl-4-amino-N-ethyl-N-(β-methane sulfonamido ethyl)aniline | 4.5 g |
| Fluorescent whitening agent (4,4'-diamino stilbene sulfonic acid derivative) | 1.0 g |
| Potassium carbonate | 27 g |
| Add water to make in total of | 1 liter |
| Adjust pH to be | pH 10.10 |
| (Bleach-fixer) | |
| Ferric ammonium ethylenediamine tetraacetate, dihydrate | 60.0 g |
| Ethylenediamine tetraacetic acid | 3.0 g |
| Ammonium thiosulfate (in an aqueous 70% solution) | 100.0 ml |
| Ammonium sulfite (in an aqueous 40% solution) | 27.5 ml |
| Add water to make in total of | 1 liter |
| Adjust pH with potassium carbonate or glacial acetic acid to be | pH 5.7 |
| (Stabilizer) | |
| 5-Chloro-2-methyl-4-isothiazoline-3-one | 0.2 g |
| 1,2-Benzisothiazoline-3-one | 0.3 g |
| Ethylene glycol | 1.0 g |
| 1-Hydroxyethylidene-1,1-diphoshonic acid | 2.0 g |
| Sodium o-phenylphenol | 1.0 g |
| Ethylenediamine tetraacetic acid | 1.0 g |
| Ammonium hydroxide (in an aqueous 20% solution) | 3.0 g |
| Fluorescent whitening agent (4,4'-diamino stilbene sulfonic acid derivative) | 1.5 g |
| Add water to make in total of | 1 liter |
| Adjust pH with sulfuric acid or potassium hydroxide to be | pH 7.0 |

With the processed Samples 1 through 14, each of the maximum density ($D_{max}$) thereof was measured by a densitometer (Model KD-7 manufactured by Konica Corp.). Further, the processed samples were allowed to stand under the high temperature and high humidity condition (at 85° C. and 60% RH) for 21 days, and the heat resistance and moisture resistance of the resulting dye images were checked up.

The heat stability and humidity stability of each dye image were indicated in terms of a dye residual percentage obtained after completing the heat and humity stability tests. The results thereof will be shown in Table 1.

TABLE 1

Comparative coupler a

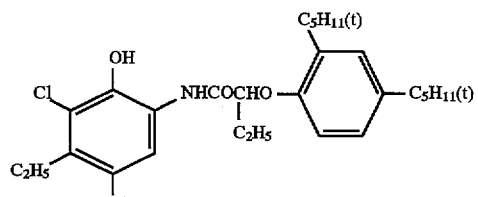

Comparative coupler b

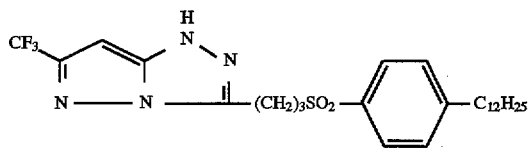

(The coupler disclosed in JP OPI Publication No. 64-544/1989)

| Sample No. | Coupler used | Color developability, Dmax | Dye residual ratio (%) Heat & humidity stability |
|---|---|---|---|
| 1 | Comparative a | 2.30 | 81 |
| 2 | Comparative b | 1.79 | 94 |
| 3 | Inventive I-1 | 2.48 | 97 |
| 4 | Inventive I-5 | 2.51 | 98 |
| 5 | Inventive I-12 | 2.46 | 97 |
| 6 | Inventive I-6 | 2.45 | 96 |
| 7 | Inventive I-16 | 2.44 | 97 |
| 8 | Inventive I-23 | 2.50 | 98 |
| 9 | Inventive I-27 | 2.48 | 99 |
| 10 | Inventive I-32 | 2.46 | 99 |
| 11 | Inventive I-41 | 2.51 | 98 |
| 12 | Inventive I-43 | 2.50 | 99 |
| 13 | Inventive II-1 | 2.40 | 95 |
| 14 | Inventive II-13 | 2.47 | 95 |

As is obvious from the results shown in Table 1, it can be found that every sample applied with the couplers of the invention is high in Dmax and dye residual ratio and excellent in color developability and heat moisture resistance, as compared to the samples applied with the comparative couplers.

Example 2

On a paper-made support laminated with polyethylene on one side thereof and with polyethylene containing titanium oxide on the other side thereof, each of the layers having the following compositions was coated on the titanium oxide-containing polyethylene layer-side, so that Sample 15 of a multilayered silver halide photographic light-sensitive material was prepared. The coating solutions were prepared in the following manner.

Coating solution for Layer 1

Sixty (60) ml of ethyl acetate was added to 26.7 g of yellow coupler (Y-1), 10.0 g of dye-image stabilizer (ST-1), 6.67 g of dye-image stabilizer (ST-2), 0.67 g of additive (HQ-1), anti-irradiation dye (AI-3) and 6.67 g of high-boiling organic solvent (DNP), and the mixture thereof was dissolved. The resulting solution was emulsified and dispersed in 220 ml of an aqueous 10% gelatin solution containing 7.0 ml of 20% surfactant (SU-1) by making use of an ultrasonic homogenizer, so that a yellow coupler dispersed solution could be prepared. The resulting dispersed solution was mixed with a blue light-sensitive silver halide emulsion (containing 8.68 g of silver) that was prepared under the following conditions, so that a coating solution for Layer 1 could be prepared.

Coating solutions for Layers 2 through 7 were each prepared in a manner similar to the above-mentioned coating solution for Layer 1.

As a hardener, (H-1) was added to each of Layers 2 and 4 and (H-2) to Layer 7. As a coating aid, surfactants (SU-2) and (SU-3) were added thereto, so that the surface tension of the layers were controlled. The amounts thereof added to a silver halide photographic light-sensitive material will be hereinafter indicated in terms of grams per sq.meter, unless otherwise expressly stated.

The layer arrangements were as shown in the following table.

TABLE 2

| Layer | Composition | Amount ($g/m^2$) |
| --- | --- | --- |
| Layer 7 (Protective layer) | Gelatin | 1.00 |
| | DIDP | 0.05 |
| | Antistaining agent (HQ-2) | 0.002 |
| | Antistaining agent (HQ-3) | 0.002 |
| | Antistaining agent (HQ-4) | 0.004 |
| | Antistaining agent (HQ-5) | 0.002 |
| | Antimold (F-1) | 0.002 |
| Layer 6 (UV-absorption layer) | Gelatin | 0.40 |
| | UV-absorbent (UV-1) | 0.10 |
| | UV-absorbent (UV-2) | 0.04 |
| | UV-absorbent (UV-3) | 0.16 |
| | Antistaining agent (HQ-5) | 0.04 |
| | DNP | 0.20 |
| | PVP | 0.03 |
| | Anti-irradiation dye (AI-2) | 0.02 |
| | Anti-irradiation dye (AI-4) | 0.01 |
| Layer 5 (Red-sensitive layer) | Gelatin | 1.30 |
| | Red-sensitive silver chlorobromide emulsion (Em-R) | 0.21 |
| | Cyan coupler (C-1) | 0.17 |
| | Cyan coupler (C-2) | 0.25 |
| | Dye-image stabilizer (ST-1) | 0.20 |
| | Antistaining agent (HQ-1) | 0.01 |
| | HBS-1 | 0.20 |
| | DOP | 0.20 |
| Layer 4 (UV-absorption layer) | Gelatin | 0.94 |
| | UV-absorbent (uv-1) | 0.28 |
| | Uv-absorbent (UV-2) | 0.09 |
| | UV-absorbent (UV-3) | 0.38 |
| | Antistaining agent (HQ-5) | 0.10 |
| | DNP | 0.40 |
| Layer 3 (Green-sensitive layer) | Gelatin | 1.40 |
| | Green-sensitive silver chlorobromide emulsion (Em-G) | 0.17 |
| | Magenta coupler (M-1) | 0.23 |
| | Dye-image stabilizer (ST-3) | 0.20 |
| | Dye-image stabilizer (ST-4) | 0.17 |
| | DIDP | 0.13 |
| | DBP | 0.13 |
| | Anti-irradiation dye (AI-1) | 0.01 |
| Layer 2 (Intermediate layer) | Gelatin | 1.20 |
| | Antistaining agent (HQ-2) | 0.03 |
| | Antistaining agent (HQ-3) | 0.03 |
| | Antistaining agent (HQ-4) | 0.05 |
| | Antistaining agent (HQ-5) | 0.23 |
| | DIDP | 0.06 |
| | Antimold (F-1) | 0.002 |
| Layer 1 (Blue-sensitive layer) (Blue-sensitive | Gelatin | 1.20 |
| | Blue-sensitive silver chlorobromide emulsion (Em-B) | 0.26 |
| | Yellow coupler (Y-1) | 0.80 |
| | Dye-image stabilizer (ST-1) | 0.30 |
| | Dye-image stabilizer (ST-2) | 0.20 |
| | Antistaining agent (HQ-1) | 0.02 |
| | Anti-irradiation dye (AI-3) | 0.01 |
| | DNP | 0.20 |
| Support | Polyethylene-laminated paper | |

The coated amounts of silver halide emulsions were indicated as calculated in terms of silver.

TABLE 2-continued

| Layer | Composition | Amount (g/m²) |
|---|---|---|

Y-1: [structure with H₃CO, (CH₃)₃CCOCHCONH, C₄H₉—N, NHCOCHCH₂SO₂C₁₂H₂₅, CH₃]

M-1: [pyrazole structure with Cl, (t)C₄H₉, (CH₂)₃SO₂C₁₂H₂₅]

C-1: [structure with OH, Cl, C₂H₅, NHCOCHO, C₂H₅, C₅H₁₁(t), C₅H₁₁(t)]

C-2: [structure with C₅H₁₁(t), (t)C₅H₁₁, OCHCONH, C₃H₇(i), OH, Cl, NHCO, pentafluorophenyl]

ST-1: [structure with C₄H₉(t), HO, COO, C₅H₁₁(t), C₄H₉(t), C₅H₁₁(t)]

ST-2: [structure with C₂H₅, C₂H₅, NCOCH₂O, C₅H₁₁(t), C₅H₁₁(t)]

ST-3: [structure with O₂S, N, OC₁₃H₂₇(i)]

ST-4: [bisphenol structure with CH₃, C₄H₉(t), HO, CH, C₃H₇, OH, C₄H₉(t), CH₃]

TABLE 2-continued
| Layer | Composition | Amount (g/m²) |
|---|---|---|
UV-1
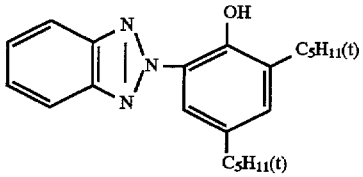
UV-2
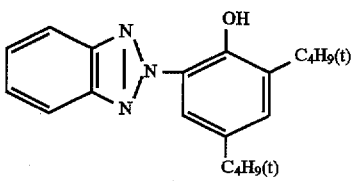
UV-3
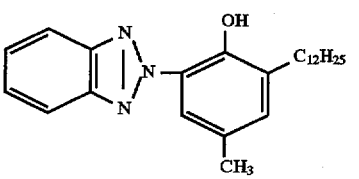
DBP = dibutyl phthalate
DOP = dioctyl phthalate
DNP = dinonyl phthalate
DIDP = diisodecyl phthalate
PVP = polyvinyl pyrrolidone
HQ-1
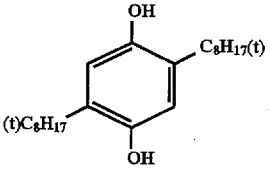
HQ-2
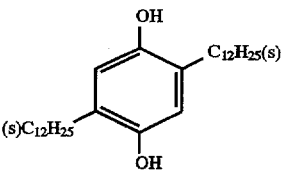
HQ-3
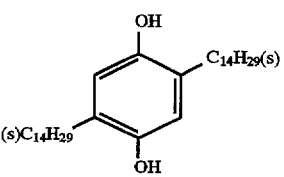
HQ-4
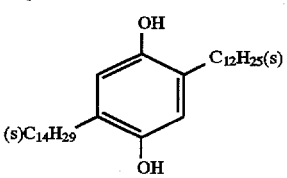

TABLE 2-continued

| Layer | Composition | Amount (g/m²) |
|---|---|---|

HQ-5

[Structure: hydroquinone derivative with two –C(CH₃)₂(CH₂)₃COOC₆H₁₃ substituents on a dihydroxybenzene ring]

HBS-1

$C_{12}H_{25}$—⟨phenyl⟩—NHSO₂—⟨phenyl⟩—CH₃

AI-1

[Pyrazolone dye structure with HOOC, =CH—CH=CH—, COOH groups; N-aryl substituents bearing SO₃K and KO₃S groups]

AI-2

[Bis-pyrazolone pentamethine dye with NHCO linkages to aryl groups bearing SO₃K substituents; N-CH₃ groups on pyrazolones]

AI-3

[Pyrazolone dye with CH₃ groups, =CH—CH=, N-aryl substituents bearing SO₃K and KO₃S]

AI-4

[Anthraquinone dye with OH, NHCH₂SO₃Na, NaO₃S, NaO₃SCH₂NH, OH, SO₃Na substituents]

SU-1

[Naphthalene with SO₃Na and (i-C₃H₇)₃ substituents]

SU-2

$NaO_3S-CHCOOCH_2CHC_4H_9$
$\phantom{NaO_3S-}|\phantom{COOCH_2CHC_4H_9}|$
$\phantom{NaO_3S-}CH_2COOCH_2CHC_4H_9$
$\phantom{NaO_3S-CH_2COOCH_2CH}|$
$\phantom{NaO_3S-CH_2COOCH_2CH}C_2H_5$ (with C₂H₅ branch on upper chain)

TABLE 2-continued

| Layer | Composition | Amount (g/m²) |
|---|---|---|

SU-3

NaO₃S—CHCOOCH₂(CF₂CH₂)₂H
         |
         CH₂COOCH₂(CF₂CF₂)₂H

H-1

C(CH₂SO₂CH=CH₂)₄

H-2

$$\text{Cl}\underset{N}{\overset{N}{\diagup}}\text{Cl}$$ (triazine structure)

F-1

(three isothiazolinone structures with Mol ratio 50%, 46%, 4%)

Preparation of Blue-sensitive silver halide emulsion

To 1000 ml of an aqueous 2% gelatin solution having been kept at 40° C., the following Solution A and Solution B were each added at the same time by taking 30 minutes with controlling the pHs thereof to be 6.5 and 3.0, respectively. Further, (Solution C) and (Solution D) were each added at the same time by taking 180 minutes with controlling the pHs thereof to be 7.3 and 5.5, respectively. The pH controls were carried out by making use of an aqueous solution of sulfuric acid or sodium hydroxide. The pAg controls were carried out by making use of the controller having the following composition. The controller is comprised of an aqueous solution of the mixture of silver halides composed of sodium chloride and potassium bromide. The proportion of the chloride ions to bromide ions was 99.8:0.2 and the concentration of the controller was 0.1 mols per liter when Solutions A and B was mixed up and 1 mol per liter when mixing Solutions C and D.

| Solution A | |
|---|---|
| Sodium chloride | 3.42 g |
| Potassium bromide | 0.03 g |
| Add water to make | 200 ml |
| Solution B | |
| Silver nitrate | 10 g |
| Add water to make | 200 ml |
| Solution C | |
| Sodium chloride | 102.7 g |
| Potassium bromide | 1.0 g |
| Add water to make | 600 ml |
| Solution D | |
| Silver nitrate | 300 g |
| Add water to make | 600 ml |

After completing the addition, a desalting treatment was carried out with an aqueous 5% solution of Demol N manufactured by Kao-Atlas Co. and an aqueous 20% magnesium sulfate solution and the desalted solution was then mixed with an aqueous gelatin solution, so that monodispersed cubic-shaped emulsion EMP-1 having an average grain-size of 0.85 μm, a variation coefficient (S/R) of 0.07 and a silver chloride content of 99.5 mol % was obtained.

The resulting emulsion EMP-1 was chemically ripened at 50° C. for 90 minutes by making use of the following compounds, so that blue-sensitive silver halide emulsion (Em-B) could be obtained.

| | |
|---|---|
| Sodium thiosulfate | 0.8 mg/mol of AgX |
| Chloroauric acid | 0.5 mg/mol of AgX |
| Stabilizer STAB-1 | 6 × 10⁻⁴ mols/mol of AgX |
| Sensitizing dye BS-1 | 4 × 10⁻⁴ mols/mol of AgX |
| Sensitizing dye BS-2 | 1 × 10⁻⁴ mols/mol of AgX |

Preparation of Green-sensitive Silver Halide Emulsion

Monodisperse type cubic-shaped emulsion EMP-2 having an average grain-size of 0.43 μm, a variation coefficient (S/R) of 0.08 and a silver chloride content of 99.5% could be obtained in the same manner as in the case of EMP-1, except that the time of adding Solution A and Solution B and the time of adding Solution C and Solution D were changed.

The resulting EMP-2 was chemically ripened at 55° C. for 120 minutes by making use of the following compounds, so that green-sensitive silver halide emulsion (Em-G) was obtained.

| | |
|---|---|
| Sodium thiosulfate | 1.5 mg/mol of AgX |
| Chloroauric acid | 1.0 mg/mol of AgX |
| Stabilizer STAB-1 | 6 × 10⁻⁴ mols/mol of AgX |
| Sensitizing dye GS-1 | 4 × 10⁻⁴ mols/mol of AgX |

Preparation of Red-sensitive Silver Halide Emulsion

Monodisperse type cubic-shaped emulsion EMP-3 having an average grain-size of 0.50 μm, a variation coefficient (S/R) of 0.08 and a silver chloride content of 99.5% was obtained in the same manner as in the case of EMP-1, except that the time of adding Solution A and Solution B and the time of adding Solution C and Solution D were changed.

The resulting EMP-3 was chemically ripened at 60° C. for 90 minutes by making use of the following compounds, so that red-sensitive silver halide emulsion (Em-R) was obtained.

| | |
|---|---|
| Sodium thiosulfate | 1.8 mg/mol of AgX |
| Chloroauric acid | 2.0 mg/mol of AgX |
| Stabilizer STAB-1 | $6 \times 10^{-4}$ mols/mol of AgX |
| Sensitizing dye RS-1 | $1 \times 10^{-4}$ mols/mol of AgX |

The variation coefficient was calculated out from the following standard deviation (S) and an average grain-size (R), $$S=[\Sigma(R_i-R)^2/\Sigma n_i]^{1/2}$$

wherein $R_i$ represents a grain size and $n_i$ represents the number of grains having an grain-size of $R_i$.

By making use of a color negative film (a Konica Color Film LV-400 manufactured by Konica Corp.) and a camera (a Konica camera FT-1 MOTOR manufactured by Konica Corp.), a color checker (manufactured by MacBeth Co.) was photographed. Successively, the photographed color-negative film was developed (with a developer CNK-4 manufactured by Konica Corp.) and the resulting negative image was printed on each of the above-mentioned samples Nos. 15 through 39 to be in the size of 82 mm×117 mm by making use of a Konica Color Printer CL-P2000 (manufactured by Konica Corp.), so that the practical prints were obtained in the same manner as mentioned above. When making every print, the printing conditions were so set as to reproduce the same gray on every print as on the color checker.

BS-1

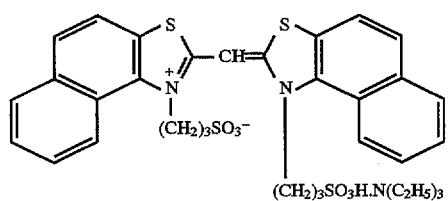

BS-2

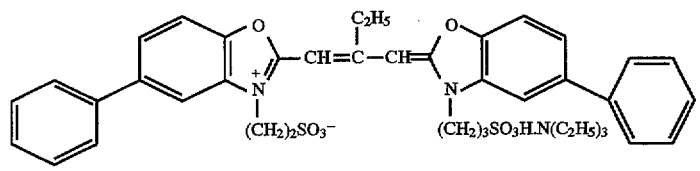

GS-1

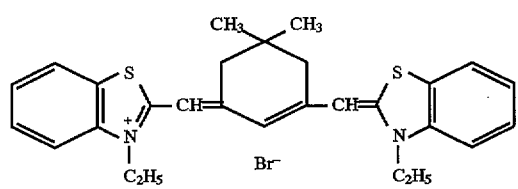

RS-1

STAB-1

Samples 16 through 39 of the invention were each prepared in the same manner as in Sample 15, except that cyan couplers (C-1) and (C-2) of Layer 5 of Sample 15 were replaced by the couplers shown in Table 3, (in which the amounts thereof added were the same mols as the total mols of the comparative couplers C-1 and C-2).

The resulting samples were each exposed to light through an optical wedge as in Example 1 and were developed. The maximum density (Dmax) of each of the red light-sensitive layers was determined.

With each of the above-mentioned samples 15 through 39, the color reproducibility thereof was evaluated in the following manner.

Regarding the resulting practical prints, the color reproducibility and black background property thereof were visually evaluated, based on five grades ranging from 1 (poor) to 5 (excellent).

The results thereof will be shown collectively in Table 3.

TABLE 3

| Sample No. | Cyan coupler | Maximum density | Color reproducibility* Cyan | Blue | Green | Black background | Remarks |
|---|---|---|---|---|---|---|---|
| 15 | C-1/C-2 | 2.49 | 3 | 3 | 3 | Excellent | Comparison |
| 16 | Coupler C | 2.10 | 3 | 5 | 3 | Insufficient | Comparison |
| 17 | Coupler d | 2.27 | 3 | 5 | 3 | Insufficient | Comparison |
| 17 | Coupler e | 2.27 | 3 | 5 | 3 | Insufficient | Comparison |
| 18 | I-3 | 2.51 | 5 | 5 | 5 | Excellent | Invention |
| 19 | I-7 | 2.54 | 5 | 5 | 5 | Excellent | Invention |
| 20 | I-9 | 2.46 | 4 | 5 | 5 | Excellent | Invention |
| 21 | I-10 | 2.47 | 5 | 5 | 5 | Excellent | Invention |
| 22 | I-13 | 2.52 | 5 | 5 | 5 | Excellent | Invention |
| 23 | I-18 | 2.54 | 4 | 5 | 5 | Excellent | Invention |
| 24 | I-20 | 2.42 | 4 | 5 | 5 | Excellent | Invention |
| 25 | I-21 | 2.49 | 4 | 5 | 4 | Excellent | Invention |
| 26 | I-25 | 2.56 | 5 | 5 | 5 | Excellent | Invention |
| 27 | I-31 | 2.50 | 5 | 5 | 5 | Excellent | Invention |
| 28 | I-35 | 2.53 | 4 | 5 | 4 | Excellent | Invention |
| 29 | I-36 | 2.49 | 4 | 5 | 4 | Excellent | Invention |
| 30 | I-38 | 2.49 | 5 | 5 | 5 | Excellent | Invention |
| 31 | I-41 | 2.59 | 5 | 5 | 5 | Excellent | Invention |
| 32 | I-42 | 2.57 | 5 | 5 | 5 | Excellent | Invention |
| 33 | I-43 | 2.54 | 5 | 5 | 5 | Excellent | Invention |
| 34 | I-47 | 2.50 | 5 | 5 | 5 | Excellent | Invention |
| 35 | II-2 | 2.46 | 4 | 5 | 4 | Excellent | Invention |
| 36 | II-4 | 2.46 | 4 | 5 | 4 | Excellent | Invention |
| 37 | II-10 | 2.47 | 3 | 5 | 4 | Excellent | Invention |
| 38 | II-16 | 2.42 | 4 | 5 | 4 | Excellent | Invention |
| 39 | II-19 | 2.40 | 4 | 5 | 4 | Excellent | Invention |

*Color reproducibility (hue, saturation):
1 (poor) - 5 (excellent)

Comparative coupler c

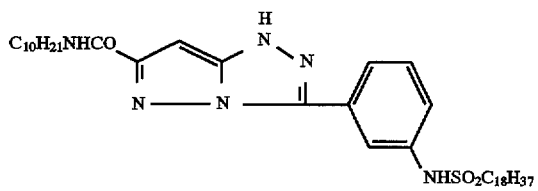

(The coupler given in JP OPI Publication No. 63-250650/1988)

Comparative coupler d

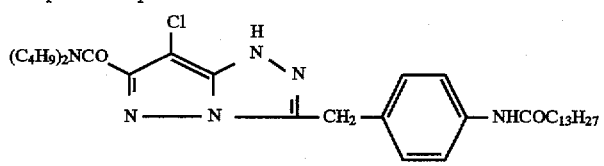

(The coupler disclosed in JP OPI Publication No. 64-544/1989)

Comparastive coupler e

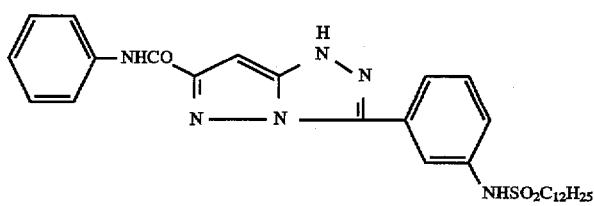

(The coupler given in JP OPI Publication No. 1-230042)

As can be seen from the Table 3, Sample No. 15 containing Comparative Couplers C-1 and C-2 was seriously unsatisfactory in color reproduction. Samples Nos. 16 and 17 each containing Comparative Couplers c and d were scarcely improved in cyan and green color reproducibility and were also insufficient in black background property because of the low maximum density, though the blue color reproducibility was apparently improved well.

In contrast to the above, the samples containing the cyan couplers of the invention, including particularly Samples No. 12 through 19, were not only excellent in reproducibility of every color, cyan, blue and green, in color developability and in black background property, but also high in the maximum density.

What is claimed is:

1. A silver halide color photographic light sensitive material comprising a support having thereon a silver halide emulsion layer containing silver halide grains, wherein said silver halide emulsion layer contains a cyan dye forming coupler represented by the following formula (1) or (2),

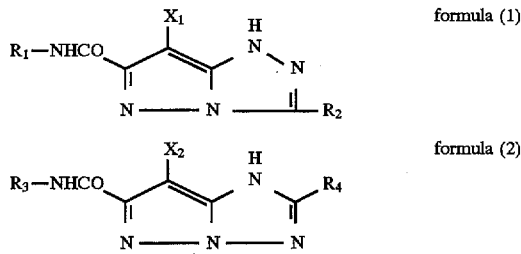

wherein $R_1$ and $R_3$ independently represents a heterocyclic group, alkoxy group, aryloxy group, heterocyclic-oxy group or

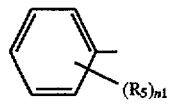

in which $R_5$ represents a substituent and $n_1$ is an integer of 1 to 5; $R_2$ and $R_4$ independently represent an aryl group and $X_1$ and $X_2$ represents a hydrogen atom or a coupling-off group.

2. The silver halide photographic material of claim 1, wherein said cyan coupler is represented by formula (3),

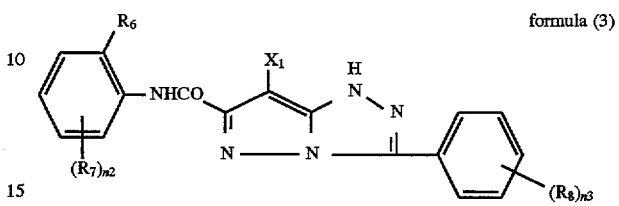

wherein $X_1$ is the same as that as defined in formula (1); $R_6$ represents a substituent; $R_7$ and $R_8$ each represent hydrogen atom or a substituent; $n_2$ is an integer of 1 to 4; and $n_3$ is an integer of 1 to 5.

3. The silver halide photographic material of claim 1, wherein said cyan coupler is contained in an amount of $1 \times 10^{-3}$ to 1 mol per mol of the silver halide grains contained in the silver halide emulsion layer.

4. The silver halide photographic material of claim 1, wherein said silver halide grains are silver chloride, silver chlorobromide or silver iodochlorobromide.

* * * * *